United States Patent [19]
Dolence et al.

[11] Patent Number: 5,650,234
[45] Date of Patent: Jul. 22, 1997

[54] ELECTROPHILIC POLYETHYLENE OXIDES FOR THE MODIFICATION OF POLYSACCHARIDES, POLYPEPTIDES (PROTEINS) AND SURFACES

[75] Inventors: Eric Kurt Dolence; Chen-Ze Hu, both of Salt Lake City; Ray Tsang, North Salt Lake; Clifton G. Sanders, Salt Lake City; Shigemasa Osaki, Sandy, all of Utah

[73] Assignee: Surface Engineering Technologies, Division of InnerDyne, Inc., Salt Lake City, Utah

[21] Appl. No.: 304,656

[22] Filed: Sep. 9, 1994

[51] Int. Cl.⁶ .................. C07K 1/00; C07K 14/00; C07K 16/00
[52] U.S. Cl. .......... 428/447; 525/54.1; 525/54.2; 525/54.21; 525/403; 525/408; 427/452; 427/2.3; 427/2.31; 427/200; 427/207; 530/350; 530/362; 530/363; 530/380; 530/381; 530/405; 530/406; 530/345; 536/21; 536/29.1
[58] Field of Search .......................... 525/408, 403, 525/54.1, 54.2, 54.21; 428/447; 427/452, 2; 527/200, 207; 530/350, 362, 363, 380, 381, 405, 406, 345; 536/21, 29.1; 548/520, 435, 465, 475, 542, 259, 296; 546/208, 243

[56] References Cited

U.S. PATENT DOCUMENTS

| | | | |
|---|---|---|---|
| 5,122,614 | 6/1992 | Zalipsky | 548/520 |
| 5,321,095 | 6/1994 | Greenwald | 525/408 |
| 5,324,844 | 6/1994 | Zalipsky | 548/520 |
| 5,349,001 | 9/1994 | Greenwald et al. | 525/408 |
| 5,510,418 | 4/1996 | Rhee et al. | 525/54.2 |

*Primary Examiner*—Frederick Krass
*Attorney, Agent, or Firm*—Lyon & Lyon LLP

[57] ABSTRACT

Several poly(ethylene glycol) mixed carbonates and their preparation are disclosed. These carbonates are synthesized by conversion of polyethylene glycol first to the chloroformate then by reaction with the hydroxyl group of N-hydroxybenzotriazole or 2-hydroxypyrimidine or N-hydroxy-2-pyrrolidinone. These mixed carbonate analogs smoothly react with amino groups in aminoglycans and protein and amino containing surfaces to form stable, hydrolysis resistant carbamate linkages.

21 Claims, 4 Drawing Sheets

1

2

3

4

5

6

For R = see Figure 1

5.0 equivalents, pH
8.5 for 30 minutes

R = H
R = SO$_3^-$Na$^+$

For R = see Figure 1

Ethanol, room temperature
5.0 equivalents N-trimethyl-
silylallylamine

ELECTROPHILIC POLYETHYLENE OXIDES FOR THE MODIFICATION OF POLYSACCHARIDES, POLYPEPTIDES (PROTEINS) AND SURFACES

FIELD OF THE INVENTION

The present invention relates to compositions for coating substrate surfaces which have polyoxyalkylene tethers attached thereto. These tethers allow bioactive compounds such as polysacchrides, polypeptides, proteins and other pharmaceuticals to be covalently attached to the surface. One such bioactive compound is heparin which renders such surfaces thromboresistant. Membrane coatings including these thromboresistant surfaces are particularly suited for use in conjunction with biomedical devices.

BACKGROUND OF THE INVENTION

Publications and other references referred to herein are incorporated herein by reference and are numerically referenced in the following text and respectively grouped in the appended Bibliography which immediately precedes the claims.

The present invention relates to the chemical modification of aminoglycans, proteins and amine coated surfaces by means of the covalent bonding of polymer chains of polyoxyalkylenes, such as polyethylene oxide (also called polyethyleneglycol) and polypropylene glycol.

Polyethylene glycol (PEG) use in biotechnology and biomedical applications continues to expand and has recently been reviewed (1). Modification of enzymes (2), RGD peptides (3), liposomes (4), and CD4-IgG glycoprotein (5) are some of the recent advances in the use of polyethylene glycol. The modification of toxicity, pharmacokinetics, biodistribution and other biofunctions are a number of the promising areas for the use of this simple polymer. Surfaces treated with PEG have been shown to resist protein deposition and have improved resistance to thrombogenicity when coated on blood contacting biomaterials (6). Accordingly, application of PEG based coatings to various polymeric materials especially with respect to "continuous" coating of microporous hollow fiber or other plastic parts would be very useful for medical devices.

Electrophilic activated polyoxyalkylenes such as PEG for continuous coating applications should satisfy the following requirements:

1. The rate of reaction between an amino group coated surface and/or an amino containing biomolecule with an electrophilically activated PEG should have an fast reaction rate under mild conditions.
2. Ideally, the electrophilically activated PEG should have an appropriate hydrolysis half-life in water at pH values of 7.5–8.5. This is especially important with respect to polymeric substrates to be coated that can not withstand exposure to organic solvents.
3. Formation of a covalent bond between an amino-containing biomolecule and the electrophilically activated PEG should be demonstrated by spectroscopic means such as nuclear magnetic resonance an/or infrared spectroscopy to demonstrate that the chemistry proceeds as expected.
4. Should organic solvents be used in the coating process, stability of the electrophilically activated PEG should be appreciable for economical reasons.
5. Reaction of the electrophilically activated PEG with the biological molecules of interest should be site directed so that crucial receptor and/or active sites are not blocked. In turn, retained biological function should be demonstrated by an appropriate assay.
6. Quality or functionality of the electrophilically activated PEG should be easily determined by rapid spectroscopic means during a manufacturing process.
7. The leaving group released upon acylation of amino groups should have high solubility in the reaction medium, minimal adsorption to the modified substrate and be non-toxic ideally.
8. The electrophilically activated PEG should have long term stability for shelf life storage purposes.
9. The covalent bond formed should be hydrolysis resistant under both the coating conditions and subsequent "actual use" conditions.

In order to covalently bond, the hydroxyl group of PEG must be "activated". This has been reported as accomplished by the use of a number of reactive functional groups including cyanurylate (7–9), tresylate (10–11), N-hydroxysuccinimide derived active esters (12–17), carbonates (18–20), imidazolyl formates (21–22), 4-dithiopyridines (23), isocyanates (24) and epoxides (25). Each of the above functional groups possess disadvantages which range from leaving group toxicity, conjugates that are prone to hydrolysis under physiological conditions and slow reaction rate in the conjugation process. Radiolabeled urethane-PEG derivative stability has been demonstrated under a variety of physiological conditions (26). The hydrolysis resistant urethane bond produced by sufficiently reactive PEG carbonates may offer considerable advantage in avoiding hydrolysis of the conjugation covalent bond. To date, literature reports on the use of PEG carbonates have focused on the modification of protein or polypeptides. Driven by our interest in developing a continuous coating process for covalently bound heparin on a microporous hollow fiber surface, we explored the reactivity of various PEG carbonates with the aminoglycan D-glucosamine and several commercially available sodium heparins.

SUMMARY OF THE INVENTION

The present invention provides for compounds having the formula:

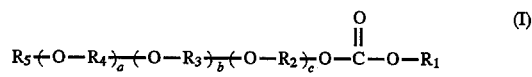

$$R_5(O-R_4)_a(O-R_3)_b(O-R_2)_c O-\overset{O}{\underset{\|}{C}}-O-R_1 \quad (I)$$

wherein $R_1$ is selected from the group consisting of an N-benzotriazole group, an N-2-pyrrolidinone group, and an 2-oxypyrimidine group; $R_2$, $R_3$ and $R_4$ are independently selected lower alkylene groups, preferably of about 2 to about 3 carbon atoms, and may be the same or different; $R_5$ is selected from the group consisting of hydrogen, methyl, a carbonyloxy-N-benzotriazole group, a carbonyl-oxy-N-2-pyrrolidinone group, and a carbonyl-2-oxypyrimidine; a is an integer from 1 to 1000 and each of b and c is an integer from 0 to 1000, and a, b and c are selected so that the sum of a, b, and c is an integer between 3 and 1000.

Preferred are compounds of formula (I) wherein each of $R_2$, $R_3$ and $R_4$ is independently —$CH_2CH_2$— or —$CH_2CH(CH_3)$— or a combination thereof.

These compounds may be homobifunctional or heterobifunctional and are suitable for modifying a variety of bioactive compounds as well as acting as a tether to link a bioactive compound to a membrane or polymeric surface.

According to a preferred aspect, the present invention further provides for the production of a modified bioactive compound such as a polysaccharide or polypeptide or other pharmaceutical that has conjugated to it via an urethane bond at least one molecule of polyoxyethylene having the structure:

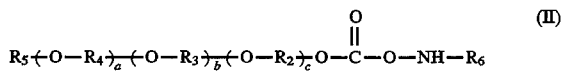

where $R_5$ is selected from the group consisting of hydrogen, methyl, a carbonyloxy-N-benzotriazole group, a carbonyloxy-N-2-pyrrolidinone group, or a carbonyl-2-oxypyrimidine group, $R_2$, $R_3$ and $R_4$ are ethylene, $R_6$ is a bioactive compound selected from an aminoglycan polysaccharide, a polypeptide, a protein or other reactive pharmaceutical compound, and a, b, and c are as defied in connection with formula (I). These modified bioactive compounds having covalently attached polyoxyalkylene groups have a variety of uses in vivo, since such substances may exhibit a reduced rate of kidney clearance and/or enhanced association with cells, and in certain instances decreased immunogenicity.

In addition, according to an additional aspect, this invention provides for a method for the covalent bonding of aminoglycan polysaccharides, polypeptides or proteins using a polyoxalkylene, such as PEG, activated with a carbonyloxy-N-benzotriazole group, a carbonyloxy-N-2-pyrrolidinone group, or a carbonyl-2-oxypyrimidine group to any surface in possession of reactive amino groups or other suitable nucleophiles. In addition, the heterobifunctional polyoxalkylenes produced thereby possess different activating groups at each end of the polyoxyalkylene chain are useful as linkers or tethers. Use of these tethers allow anchoring of the aminoglycan polysaccharides, polypeptides or proteins to other substances having an amino or appropriate nucleophile group.

Thus, the present invention includes a method for the covalent bonding of a bioactive compound selected from an aminoglycan polysacchride, a peptide, a protein or other pharmaceutically active substance to a polymeric surface using a polyoxyalkylene tether which comprises contacting a substrate having an amine-grafted polymeric surface having free amino groups with a compound of formula (I) to give a modified polymeric surface having activated polyoxyalkylene groups covalently bonded thereto; and contacting the modified polymeric surface with the bioactive compound.

According to an especially preferred aspect, the present invention provides a coating which comprises a membrane formed from the plasma polymerization of hydrocyclosiloxane monomer of the general formula:

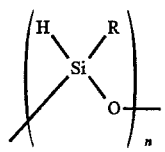

where R is an aliphatic group having 1 to about 5 carbon atoms and n is an integer from 2 to about 10, covalently linked by a carbamate linkage to one end of a polyoxyalkylene tether wherein the tether is covalently linked at its other end by a carbamate linkage to a bioactive molecule. Where the bioactive molecule is selected from compounds having antithrombotic or thrombolytic properties such as heparin, tissue plasmogen activator, streptokinese, prostaglandins and antiplatelet drugs, coatings having enhanced thrombo-resistance are provided. According to an alternate preferred aspect, the bioactive compound is a metal chelator such as deferoxamine.

Coatings prepared from plasma polymerization of a hydrocyclosiloxane monomer selected from the group consisting of 1,3,5,7-tetramethylhydrocyclotetrasiloxane, 1,3,5,7,9-pentamethylhydrocyclopentasiloxane, 1,3,5,7,9,11-hexamethylhydrocyclohexasilosane, and a mixture of 1,3,5,7,9-pentamethylcyclopentasiloxane and 1,3,5,6,9,11-hexamethylcyclohexasiloxane monomers are expecially preferred.

DETAILED DESCRIPTION OF THE INVENTION

The present invention provides several carbonate based polyalkylene oxides 1, 2, and 3 (see FIG. 1) having the general formula:

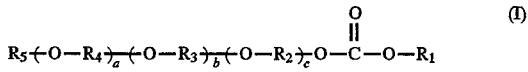

wherein $R_1$ is an N-benzotriazole group, an N-2-pyrrolidinone group, or an 2-oxypyrimidine group; $R_2$, $R_3$ and $R_4$ are independently selected lower alkylene groups, and may be the same or different; $R_5$ is selected from hydrogen, methyl, a carbonyloxy-N-benzotriazole group, a carbonyloxy-N-2-pyrrolidinone group, or a carbonyl-2-oxypyrimidine group; a is an integer between 1 and 1000; and each of b and c is an integer between 0 and 1000, such that the sum of a, b, and c is between 3 and 1000. Suitable lower alkylene groups include those having about 2 to about 3 carbon atoms. Preferred are compounds of formula (I) where $R_2$, $R_3$ and $R_4$ is —($CH_2CH_2$)— or —$CH_2CH$ ($CH_3$)— or any combination thereof. More preferably $R_2$, $R_3$ and $R_4$ are ethylene. According to a preferred aspect a, b, and c are selected so as to give a molecular weight for the PEG moiety of about 500 to about 20,000, more prpeferably from 3000 to 4000.

Preferred Polyoxyalkylene Analogs

Figure 1:
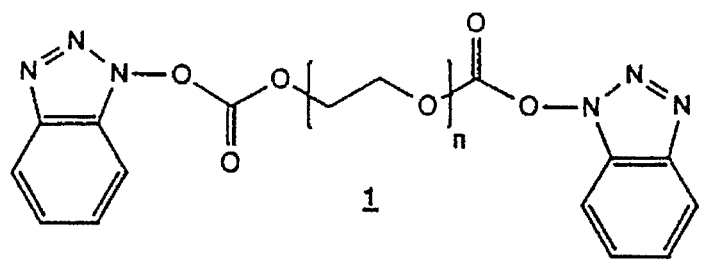
FIG. 1 depicts certain electrophilic PEG analogs according to the present invention.
Figure 1:
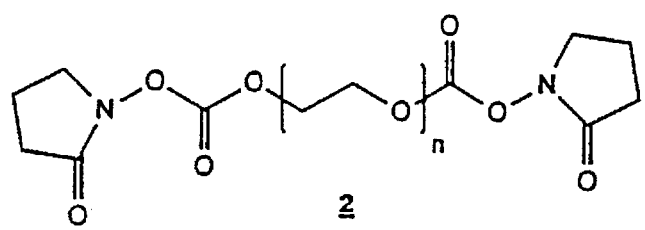
Figure 1:
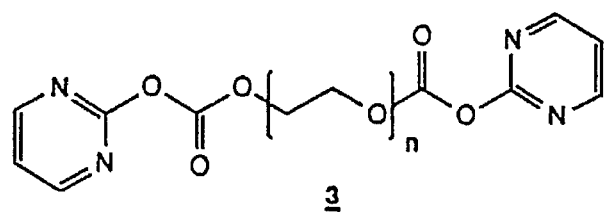
Figure 1:
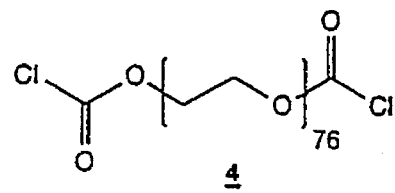
Figure 1:
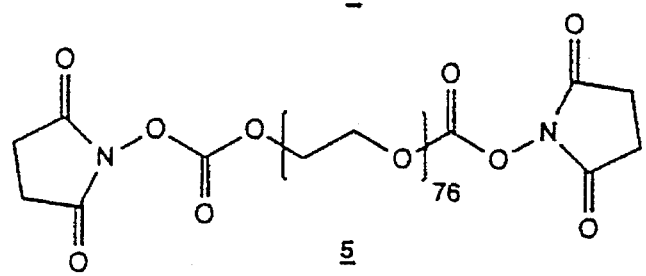
Figure 1:
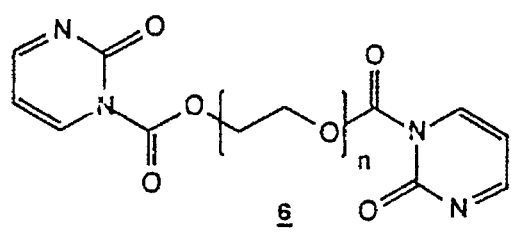

According to one aspect, this invention is directed to the synthesis and use of the new carbonate PEG analogs, which are depicted in FIG. 1 as 1, 2 and 3 and include polyoxyethylene bis-(2-hydroxypyrimidyl) carbonate 1, polyoxyethylene bis-(N-hydroxybenzotriazoyl) carbonate 1, polyoxyethylene bis-(N-hydroxy-2-pyrrolidinonyl) carbonate 2 for the modification and surface binding of aminoglycan polysaccharide or protein. According to a preferred aspect, chain length of the PEG portion is selected so as to correspond with a molecular weight of about 500 to about 20,000, more preferably from about 3000 to about 4000.

Figure 2:
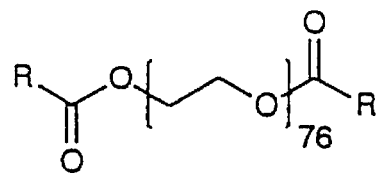
FIG. 2 depicts a reaction scheme of a PEG analog of the present invention with D-glucosamines and N-trimethylsilylallylamine.
Figure 2:
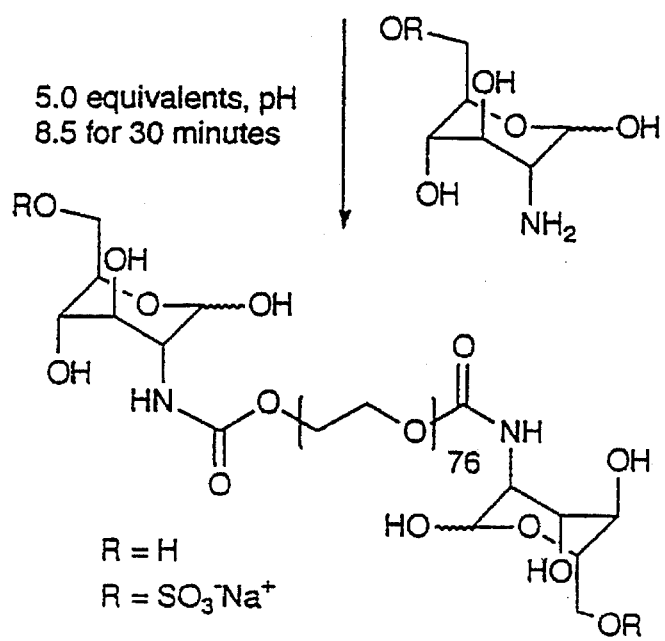
Figure 2:
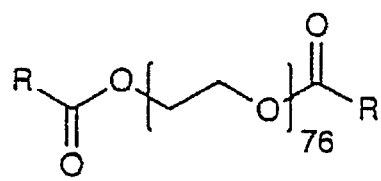
Figure 2:
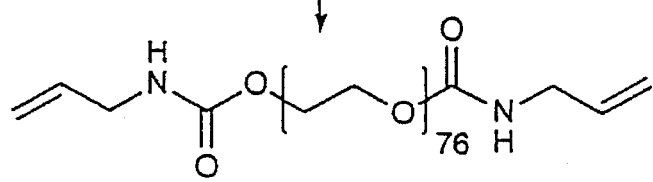
Figure 3:
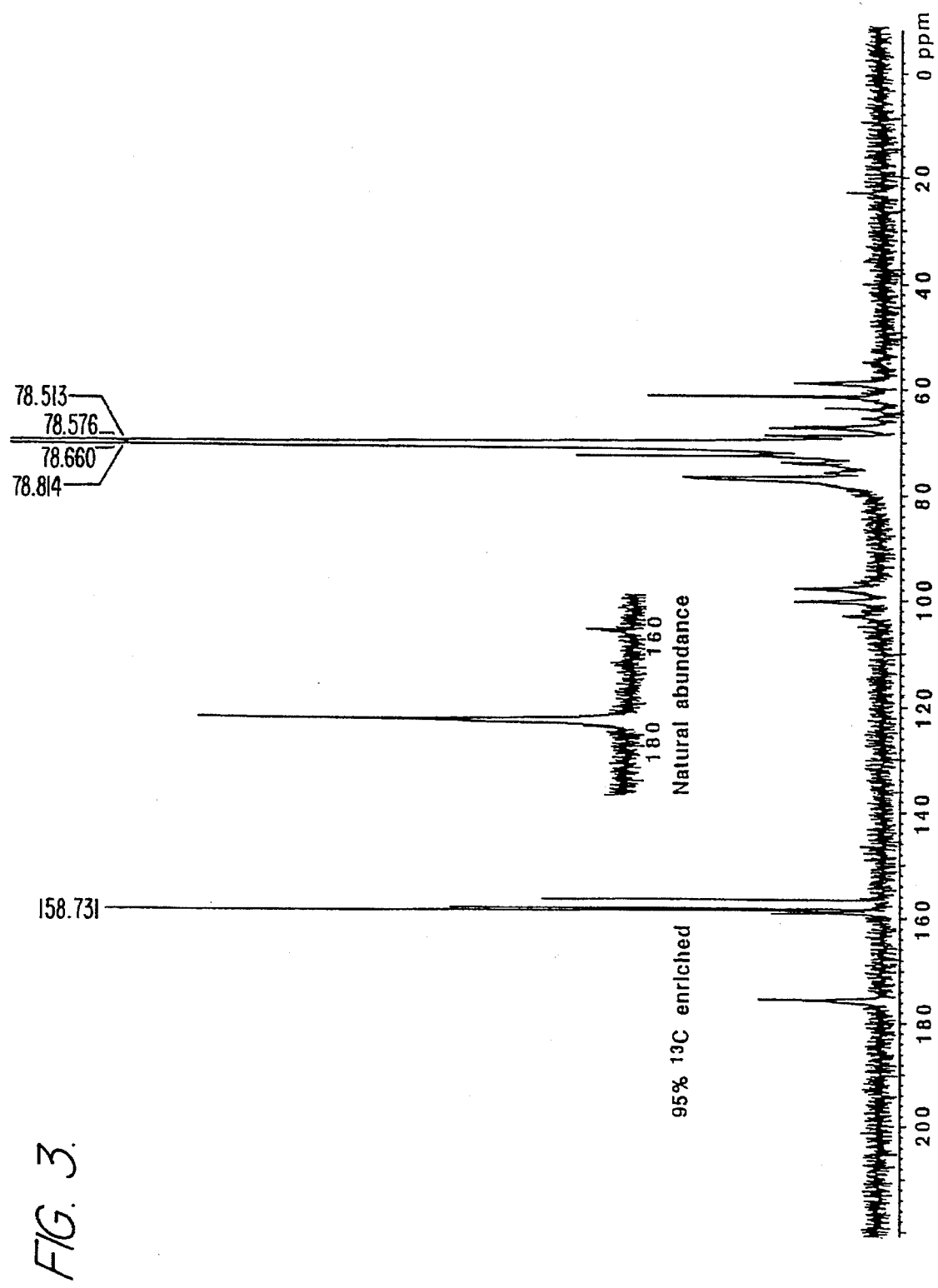
FIG. 3 depicts natural abundance (inset) and 95% $^{13}C$ enriched PEG 1—heparin conjugate Carbon NMR spectrum.

Amino group covalent bonding of the carbonates 1, 2, 3, the PEG chloroformate 4 and the N-hydroxysuccinimide derived PEG carbonate 5 (See U.S. Pat. No. 5,122,614 to Zalipsky) may be conveniently demonstrated using $^{13}C$ nuclear magnetic resonance spectroscopy coupled with the synthesis of $^{13}C$ enriched carbonate PEG analogs. Dissolution of a protein such as human serum albumin or the aminoglycans such as D-glucosamine, D-glucosamine-6-sulfate or sodium heparin, in water at pH 8.5 followed by addition of solid carbonate PEG at ambient room temperature for 30 minutes followed by ultrafiltration (Human serum albumin-PEG conjugate and sodium heparin used a 10,000 mw cut-off membrane and a 500 mw cut-off membrane for D-glucosamine and D-glucosamine-6-sulfate) afforded after lyophilization white solids. Reaction was also conducted using N-trimethylsilylallylamine in ethanol (See FIG. 2). These solids were characterized using 1H and 13C nuclear magnetic resonance for signs of urethane bonding (See FIG. 3 and Tables 1 and 4).

The approximate half-life of each of the PEG carbonates at pH 7.5–8.6 was determined using FT-infrared spectroscopy (See Table 2). Hydrolysis could not be determined for poly(oxyethylene) bis-(2-hydroxypyrimidyl) carbonate 3 since the N-migration product 6 predominated in the absence of an amino nucleophile. Analog 2 demonstrated extended half-life in water when compared to 1 or 5. This extended lifetime in water will prove useful in coating plastic parts that can only withstand aqueous coating conditions. Alcoholic solvents such as methanol and ethanol rapidly react with 1 forming the alkylcarbonate. However, excellent stability of 1 has been demonstrated for up to 6 months in dichloromethane unprotected from atmospheric moisture. Carbonates 2 and 3 as well as 5 have excellent stability in ethanol as monitored by $^1H$ NMR spectroscopy.

Since the aminoglycan such as heparin and other proteins and peptides are substrates for modification, heparin amino content was determined using the fluoroprobe fluorescamine. Various commercially available and chemically modified heparins were analyzed for primary amino content (See Table 3). All heparins examined revealed sufficient amino groups available for chemical modification as demonstrated by synthesis of 95% $^{13}C$ enriched carbonates and reaction with various heparins (Table 4).

Figure 4:
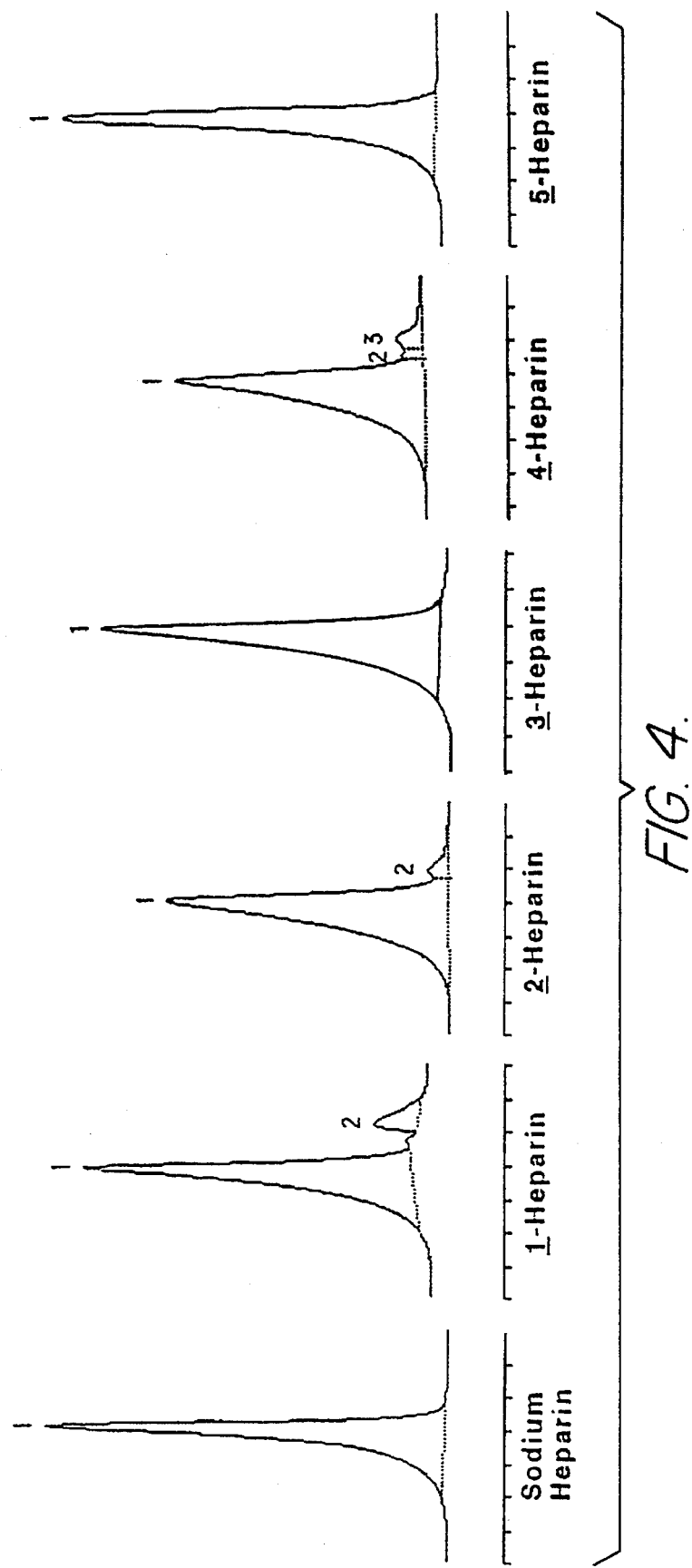
FIG. 4 depicts gel filtration high pressure liquid chromatograms of stodium heparin and PEG conjugates derived from 1, 2, 3, 4 and 5.

Size exclusion HPLC chromatography was utilized in the case of sodium heparin to determine the degree of incorporation of PEG into the polysaccharide chain. (See Table 4 and FIG. 4). Based on retention times when compared to the starting heparin, incorporation of PEG into the heparin was small in line with the number of amino groups present. Formation of carbonate groups between PEG and heparin hydroxyl groups however, can not be ruled out based on the $^{13}C$ NMR data.

Inhibition of Factor X activity in the presence of Antithrombin III ("AD") was demonstrated for the PEG-urethane-heparin conjugates. The ability of the conjugates to inhibit Factor X in the presence of Antithrombin III is decreased by PEG conjugation. Sufficient activity remains, indicating that the AT III binding site has not totally disrupted.

A tetramethylcyclotetrahydrosiloxane plasma deposited, N-trimethylsilylallylamine plasma grafted microporous hollow fiber was treated with these PEG carbonates and evaluated. Fiber was coated with polyoxyethylene bis-(N-hydroxybenzotriazolyl) carbonate 1 (solvent: dichloromethane, dwell time 10 minutes), a dichloromethane wash, followed by treatment with a pH 8.5 solution of sodium Dowex cation exchange treated sodium heparin (dwell time 10 Minutes) and a water wash. Ability to inhibit Factor X in the presence of AT III was evaluated for the fiber surface using the chromogenic substrate S-2222. Surface activity relative to the USP K2 heparin standard ranged from 7.8–14.0 milliInternational units per $cm^2$ (Table 5).

Preferred Polyoxyalkylene Modified Membranes and Coatings

According to a preferred aspect, polyoxyalkylene modified polymeric membranes or coatings are provided that comprise a membrane or coating on a substrate formed from the plasma polymerization of a hydrocyclosiloxane monomer of the general formula

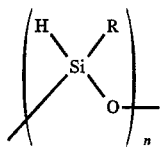

where R is an aliphatic group having 1 to about 5 carbon atoms and n is an integer from 2 to about 10, covalently linked by a carbamate linkage to one end of a polyoxyalkylene tether wherein the tether is covalently linked at its other end by a carbamate linkage to a bio-active molecule.

Commonly assigned U.S. patent application Ser. No. 08/152,176, "Hydrocyclosiloxane Membrane Prepared by Plasma Polymerization Process", filed Nov. 12, 1993, and now U.S. Pat. No. 5,463,010 the disclosure of which is incorporated by reference herein, describes preferred membranes and their preparation. The commonly assigned and concurrently filed U.S. patent application Ser. No. 08/305, 461 "Plasma Grafting of Surfaces Using N-protected Amines", filed Sep. 9, 1994, describes preferred N-protected amines and methods for their use in plasma grafting to give amine grafted membranes. These amine grafted membranes may then be conveniently reacted with the electroplytic carbonatepolyoxyalkylenes described herein to give polyoxyalkylene modified membranes or coatings. In turn, these may be reacted with appropriate bioactive compounds to give the polyoxyalkylene modified membranes or coatings having a polyoxyalkylene tether linking the bioactive compound to the membrand or coating.

According to an expecially preferred aspect, the bioactive molecule is heparin and the resulting membrane or coating has demonstrated improved thromboresistance. Such membranes or coatings are suitable for use in biomedical devices, including intravascular oxygenators.

To assist in understanding the present invention, the following examples are included which describe the results of a series of experiments. The following examples relating to this invention should not, of course, be construed as specifically limiting the invention and such variations of the invention, now known or later developed, which would be within the purview of one skilled in the art are considered to fall within the scope of the present invention as hereinafter claimed.

EXAMPLE 1

Synthesis of Poly(oxyethylene)bis-(N-hydroxybenzotriazolyl) Carbonate 1—A General Synthesis Procedure for PEG Carbonates A toluene azeotroped solution of polyethylene glycol MW 3350 (1000 grams, 0.299 mol) in 2 liters of warm toluene under nitrogen was transferred by canula slowly over 1 hour to a 500 mL solution of phosgene (Caution: Use proper ventilation) in toluene (0.965 mol) and solid sodium carbonate (63.6 g, 0.600 mol) at 0° C. The reaction mixture was stirred for 2 hours under a nitrogen environment. The ice bath was drained, a water aspirator was attached and vacuum applied with vigorous stirring. The bath was filled with warm water and the vacuum continued for 30 minutes. The solution was diluted with 2 liters of anhydrous dichloromethane to aid in filtration and quickly filtered through a coarse porosity sintered glass funnel. The solution of crude chloroformate was concentrated by rotary evaporation with a water bath temperature of 40°–42° C.

The resulting semisolid was immediately dissolved in 2.5 liters of dry acetonitrile and transferred to a 5 liter 3-neck round bottom flask under a nitrogen environment. This flask was cooled down to 0°–3° C. with vigorous stirring as measured by an internal thermometer. The N-hydroxy compound, N-hydroxybenzotriazole monohydrate (130.4 g, 0.965 mol) was dissolved into 100 mL dry acetonitrile and triethylamine (135 mL, 0.965 mol). This solution was added dropwise to the cooled solution of chloroformate at such a rate that the internal temperature did not exceed 5° C. The reaction was stirred for 15 minutes, then the mixture was filtered through a coarse porosity sintered glass funnel to remove triethylamine hydrochloride. The reaction mixture was concentrated by rotary evaporation to remove the acetonitrile with the water bath not exceeding 40° C.

The thick oil/suspension was then dissolved in 2 liters of dichloromethane and 2 liters of distilled deionized water. The mixture was poured into a separatory funnel and the aqueous phase extracted with three 1 liter portions of dichloromethane. The pooled organic phases were washed successively with 2.5% aqueous HCl, 1M aqueous sodium bicarbonate and water. The organic phases were dried over anhydrous magnesium sulfate and filtered by suction through a coarse porosity sintered glass funnel. The dichloromethane was removed by rotary evaporation affording the crude carbonate as an oil. This oil was poured into 2 mechanically stirred, 5 liter Erlenmeyer flasks (approximately on half of the oil in each flask) each containing 4 liters of ice cold ethyl acetate. Dichloromethane (100 mL) was used to rinse the flask of carbonate which was poured into the ethyl acetate. Precipitation of the carbonate was aided by placing the flasks in an explosion proof freezer overnight. The solid carbonate was then collected by suction filtration, washed with a minimum of ice cold ethyl acetate and dried in vacuo (916 g). The filtrate can be reduced in vacuo and precipitated in ethyl acetate to afford a second crop of carbonate. The yield was 94% of a granular off-white solid.

Spectral data: IR (TF, NaCl) 2942, 2885, 1773 and 1754 (carbonate carbonyls), 1494, 1465, 1434, 1359, 1344, 1302, 1281, 1258, 1241, 1148, 1113, 1061, 962, 843, 767, 748 $cm^{-1}$; $^1H$ NMR ($CDCl_3$) δ 8.22 (ddd, J=1, 2 and 8.4 Hz, 1H, aromatic H), 8.00 (ddd, J=1, 2 and 8.4 Hz, 1H, aromatic H), 7.79 (ddd, J=8.4 and 2 Hz, 1H, aromatic H), 7.56 (ddd, J=8.4 and 2 Hz, 1H, aromatic H), 4.69 (pentet, J=3.3 and 9.6 Hz, four PEG methylene protons a to the carbonate oxygen), 4.58 (pentet, J=3.3 and 9.6 Hz, four PEG methylene protons a to the carbonate oxygen—possible conformational isomer), 4.28 (very small pentet due to high molecular weight PEG carbonate), 3.92 (pentet, J=3.6 and 9.3 Hz, four PEG methylene protons b to the carbonate oxygen), 3.88 (m, $^{13}C$ isotope side band), 3.64 (large singlet, PEG backbone), 3.40 (m, $^{13}C$ isotope side band); $^{13}C$ NMR ($CDCl_3$) d 146.90 (carbonate carbonyl); 113.03, 132.44, 132.37, 125.98, 115.35, 114.90 (aromatic carbons); 70.47, 70.24 (PEG backbone); 68.12, 67.65.

EXAMPLE 2

Procedures for the Synthesis of Poly(oxyethylene) bis-(N-hydroxy-2-pyrrolidinonyl) Carbonate 2

The title compound was prepared by following the general procedure described in Example 1, using N-hydroxy-2-pyrrolindinone as the N-hydroxy compound in place of N-hydroxy benzotriazole monohydrate. Yield was 93%.

Spectral data: IR (KBr) 2880, 1790, 1732, 1465, 1358, 1278, 1113, 946, 842 $cm^{-1}$; $^1H$ NMR ($CDCl_3$) δ 4.40 (pentet, J=2.7 and 9.6 Hz, four PEG methylene protons a to the carbonate oxygen), 3.88 (m, $^{13}C$ isotope side band), 3.76 (pentet, J=3.0 and 9.6 Hz, four PEG methylene protons b to the carbonate oxygen), 3.64 (large singlet, PEG backbone and 2H superimposed, $NCH_2CH_2CH_2CO$), 3.40 (m, $^{13}C$ isotope side band), 2.40 (t, J=7.2 and 8.4 Hz, 2H, $NCH_2CH_2CH_2CO$), 2.10–2.22 (m, 2H, $NCH_2CH_2CH_2CO$); $^{13}C$ NMR ($CDCl_3$) d 170.41 ($NCH_2CH_2CH_2CO$), 152.76 (carbonate carbonyl), 70.14 (PEG backbone), 68.56, 68.07, 46.39 ($NCH_2CH_2CH_2CO$), 26.43 ($NCH_2CH_2CH_2CO$), 14.95 ($NCH_2CH_2CH_2CO$).

EXAMPLE 3

Procedure for the synthesis of poly(oxyethylene) bis-(2-hydroxypyrimidyl) carbonate 3

The chloroformate of PEG 3350 4 was synthesized using the general methods described in Example 1 for the synthesis of carbonate 1, using 2-hydroxypyrimidine hydrochloride as the N-hydroxy compound in place of N-Hydroxy benzotriazolemonohydrate as follows.

The crude PEG chloroformate was dissolved in 2.0 L of chloroform and placed under a nitrogen environment. To this solution was added solid 2-hydroxypyrimidine hydrochloride (170 g, 1.257 mol). Tributylamine (300 mL, 1.247 mol) was added dropwise. The reaction mixture was brought to reflux and monitored for reaction completion using proton NMR in $CDCl_3$. Monitoring was crucial to ensure that the N-migration product 6 is minimized. At the time that proton NMR revealed all chloroformate had been consumed, the reaction mixture was cooled in a ice bath to precipitate out the excess 2-hydroxypyrimidine hydrochloride. The cold reaction mixture was then filtered through a coarse porosity sintered glass funnel into three 5 liter suction flasks containing ice cold diethylether (3 liters each) which induced precipitation of the carbonate product. The solid was collected by filtration. At this point the solid was contaminated with tributylamine and its hydrochloride salt. These contaminates were removed from the solid by packing the solid in a medium pressure liquid chromatography column and pumping ice cold diethylether through the column until all signs of tributylamine and its hydrochloride salt were absent as monitored by proton NMR. The diethylether used can be recycled into the extraction process by simple rotary evaporation. Once all tributylamine and its hydrochloride salt were removed, the solid was dried in vacuo affording a light yellow solid.

Spectral data: IR (TF, NaCl) 2885, 1775, 1735, 1630, 1465 $cm^{-1}$; $^1H$ NMR (CDCl3) δ 8.54 (d, J=4.8 Hz, 2H, pyrimidyl), 7.16 (t, J=4.8 Hz, 1H, pyrimidyl), 4.10–4.20 (m, four PEG methylene protons a to the carbonate oxygen), 3.68 (m, $^{13}C$ isotope side band), 3.57 (large singlet, PEG backbone), 3.20 (m, 13C isotope side band); 13C NMR (CDCl3) d 159.8, 159.6, 151.29 (carbonate carbonyl), 119.28, 69.93 (PEG backbone), 67.79, 66.45.

Urethane N-rearrangement product—Polyoxyethylene bis-(1-pyrimidyl-2-one) carbamate 6: $^1H$ NMR ($CDCl_3$) δ 9.19 (d, J=8.1 Hz, 1H, pyrimidyl), 7.62 (d, J=14.1 Hz, 1H, pyrimidyl), 5.69 (dd, J=8.1 and 14.1 Hz, 1H, pyrimidyl), 4.10–4.20 (m, four PEG methylene protons α to the carbonate oxygen), 3.68 (m, $^{13}C$ isotope side band), 3.57 (large singlet, PEG backbone), 3.20 (m, $^{13}C$ isotope side band).

EXAMPLE 4

Determination of hydrolysis half-life ($t_{1/2}$) of PEG carbonates

To a flask of 100 mL of pH 8.5 distilled water using the pH stat (1.0M aqueous sodium hydroxide) was added 5.0 grams of solid PEG carbonate with vigorous stirring. 10 mL samples were removed at times of 5, 15, 30, 60, 90, 120, 180 and 320 minutes. Each sample was immediately extracted with 25 mL of dichloromethane. The organic phase was dried over anhydrous magnesium sulfate, filtered and evaporated. The residue was applied to a wafer of sodium chloride and an FTIR was obtained. The intensity of the carbonate carbonyl peak was measured compared with the PEG backbone peak located at approximately 1462 $cm^{-1}$. The ratio of peak intensities was plotted versus time. The time at which the carbonate peak intensity had decreased by 50% as compared with the starting carbonate was determined to be the approximate hydrolysis half life at pH 8.5.

EXAMPLE 5

Coupling of PEG carbonates with D-glucosamine, sodium heparins and human serum albumin (HSA)

A solution of 288 mg (1.33 mmol) of D-glucosamine hydrochloride in 10 mL of distilled deionized water was adjusted to pH 8.5 with the aid of a pH star (Metrohm Model 702) using 0.1M aqueous sodium hydroxide. To this solution was added the PEG carbonate (0.133 mmol) as a solid and the pH star was allowed to bring the pH back to 8.5. The mixture was stirred for 30 minutes, then the product isolated by extraction with dichloromethane or by ultrafiltration (Amicon membrane YM1: mwco 500) and lyophilization. Yields were higher for product purification and isolation by ultrafiltration.

Sodium heparin reaction with PEG carbonates were conducted in a similar fashion except equal weights of PEG carbonate and sodium heparin were used to ensure complete acylation of all available free amino groups. The crude reaction mixture was ultrafiltrated (Amicon YM1 10,000 mwco) with distilled deionized water using 1.5 liters for every 1.0 gram of PEG carbonate used.

EXAMPLE 6

Coupling of PEG Carbonates to an Amine Grafted Polymeric Surface

The PEG carbonates of the present invention may be conveniently coupled to plasma amine grafted tetramethylhydrocyclotetrasiloxane KDF-190 polypropylene fiber (such as that described in the commonly assigned and concurrently filed U.S. patent application "Plasma Grafting Methods and Compounds") according to the following method:

The amine-grafted coated fiber is either dip coated or pulled through a solution of the desired PEG carbonate in dichloromethane having a PEG carbonate concentration of about 3 to about 10% (about 4.25% is preferred). For the dip procedure, contact time is about 10 minutes. For the pull procedure, dwell time is about 10 minutes. The fiber is then removed and washed with dichloromethane. for the pull through process (continuous coating process) a modular coating machine may be used.

EXAMPLE 7

Coupling of PEG Carbonate Coupled Fiber to Heparin

Carbonate coupled fiber prepared according to Example 6 may be conveniently coupled to heparin using methods similar to those described in Example 5.

For example, a PEG carbonate coupled fiber can be passed through a tank of heparin solution, across a drying area and then wound back on a spool.

EXAMPLE 8

Determination of heparin mediated Antithrombin III inhibition of Bovine Factor X using the chromogenic substrate S-2222

Determination of heparin activity of the coated fibers was accomplished using a modification of the commercially available Coatest® assay kit sold by Helena Laboratories. These modifications included sonication during the incubation period and acid-stop methodology using acetic acid. Sonication during the incubation increased reproducibility with fiber surface bound samples yet had no effect on solution soluble samples. Calibration standardization was relative to the commercially available United State Pharmacopeia K2 heparin standard. Absorbance change was monitored at 405 nm. Solution heparin and heparin-PEG sample activity was expressed as IU/mg of solid. Surface heparin activity was expressed as $mIU/cm^2$ surface area. Plasma amine grafted tetramethylcyclotetrasilooxane KDF-190 polypropylene fibers coupled to heparin using one of the PEG carbonates described herein were found to have surface heparin activity which ranged from about 7 to about 14 $mIU/cm^3$.

TABLE 1

Screening of PEG analogs for acylation with amines: yield[a] and 1 bond $^{13}C$ chemical shift (ppm)[b]

| PEG Analog | D-glucosamine | D-glucosamine 6-sulfate | N-TMS-al |
|---|---|---|---|
| 1 | 55%, 159.4, 159.1 | 159.4, 159.2, 159.1, 156.6, 155.0 | 74% |
| 2 | 48%, 159.4, 159.1 | 159.4, 159.1 | 48% |
| 3 | 90%, 158.7, 158.4 | 159.4, 159.1, 156.8 | 98% |
| 4 | 62%, 159.4, 159.1 | n/a[c] | n/a |
| 5 | 71%, 159.4, 159.1 | 159.4, 159.1 | n/a |

[a]Yields vary from 40–60% when product isolated by aqueous workup using dich 100% when isolated by ultrafiltration (500 MW cutt-off) and lyophillization
[b]Chemical shift of other amine urethane carbonyls: ammonia - 160.11 ppm; glyc
[c]n/a—not attempted

TABLE 2

Approximate half-life (minutes) of PEG carbonates 1, 2, 3 and 5 as determined by FTIR at pH 8.5

| PEG Analog | Approximate $t_{1/2}$ hydrolysis |
|---|---|
| 1 | 15 |
| 2 | 132 |
| 3 | n/a |
| 5 | 47 | n/a: N-migration product 6 predominates in absence of an amino nucleophile

TABLE 3

Fluorescamine analysis of various heparins for primary free amines

| Heparin sample | Glucosamine equiv. (nmol/μg (std dev)) |
|---|---|
| Diosynth[a] | 0.055 (±0.003) |
| Diosynth (dialyzed)[b] | 0.053 (±0.006) |
| EDC/diamine modified[c] | 0.062 (±0.005) |
| N-deacetylated/ hydrazide modified[d] | 0.144 (±0.023) |
| H+ Dowex treated[e] | |
| 2.5 mL/minute | 0.064 (±0.002) |
| 5.0 mL/minute | 0.065 (±0.003) |
| N-desulfated modified[f] | |
| 15 minutes, 95° C. | 0.340 (±0.026) |
| 1.5 minutes, 95° C. | 0.047 (±0.006) |
| 15 minutes, 20° C. | 0.043 (±0.004) |
| 15 minutes, 0° C. | 0.042 (±0.005) |

[a]As purchased from the bottle, average of three triplicate runs
[b]Dialyzed using Spectra/Por CE dialysis tubing mwco 1000 against distilled deionized water, average of three triplicate runs
[c]10.0 grams Diosynth heparin, 32.6 mmol EDC, 326 mmol diamine
[d]Diosynth heparin, 6 hours at 100° C., hydrazine and 1% w/v hydrazine sulfate
[e]Fractions tested for toluidine blue and immediately neutralized using 0.1M NaOH
[f]Diosynth heparin, sulfuric acid (0.23N)

TABLE 4

$^{13}$C NMR chemical shift (ppm) of natural abundance and 95% $^{13}$C e Heparin and PEG-HSA Urethane conjugates, GF-HPLC and Heparin mediated of Factor Xa activity

| Compound | Urethane $^{13}$C signals observed for: Natural abundance | 95% $^{13}$C enriched | GF-HPLC[a] $t_r$ (minutes) |
|---|---|---|---|
| Sodium Heparin[b] | — | — | 12.00 |
| 1-Na+ heparin[b] | 158.7, 156.6 | 159.2, 158.7, 158.3, 156.6 | 11.85 |
| 2-Na+ heparin[b] | 158.7, 156.6 | 159.2, 159.1, 158.7, 158.3, 156.6, 155.1 | 11.92 |
| 3-Na+ heparin[b] | 159.3, 158.7, 156.3 | 160.1, 159.3, 159.2, 158.7, 158.6, 156.7, 156.6, 155.2, 155.1, 153.9, 153.3 | 11.85 |
| 4-Na+ heparin[b] | 159.1, 158.9, 158.6 | 159.2, 158.7, 156.6, 156.4, 155.3 | 11.82 |
| 5-Na+ heparin[b] | 159.1, 158.7 | 159.3, 159.0, 158.9, 158.7, 156.5, 154.0 | 11.91 |
| 5-HSA | none | 159.2 (Broad) | n/a[c] |
| 1-HSA | none | 159.2 (Broad) | n/a |

[a]Gel filtration HPLC and heparin activity testing conducted on natural abundance$^{13}$C ( triplicute
[b]Diosynth,
[c]n/a—not attempted

TABLE 5

Antithrombin III mediated Factor Xa inhibition by surface bound heparin[a].

| Coated fiber run number | K2 heparin activity - mIU/cm² (std dev) |
|---|---|
| 1 | 7.8(4.1) |
| 2 | 9.0(3.5) |
| 3 | 14.0(3.1) |
| 4 | 11.8(4.3) |
| 5 | 10.4(4.8) |

[a]Control fiber using a tetramethyltetrahydrocyclosiloxane coated surface typically afforded values in the range of 0.00–0.3 mIU/cm²

BIBLIOGRAPHY

1. Poly(ethylene glycol) Chemistry: Biotechnical and Biomedical Applications (J. M. Harris, Ed.), Plenum Press New York 1992.
2. Chiu, H.; Zalipsky, S.; Kopeckova, P.; Kopacek, J. (1993) Enzymatic Activity of Chymotrypsin and Its Poly (ethylene glycol) Conjugates toward Low and High Molecular Weight Substrates, Bioconjugate Chem. 4, 290–295.
3. Braatz, J. A.; Yasuda, Y.; Olden, K.; Yamada, K. M.; Heifetz, A. H. (1993) Functional Peptide-Polyurethane Conjugates with Extended Circulatory Half-Lives, Bioconjugate Chem. 4, 262–267.
4. Zalipsky, S. (1993) Synthesis of an End-Group Functionalized Polyethylene Glycol-Lipid Conjugate for preparation of Polymer-Grafted Liposomes, Bioconjugate Chem. 4, 296–299.
5. Chamow, S. M.; Kogan, T. P.; Venuti, M.; Gadek, T.; Harris, R. J.; Peers, D. H.; Mordenti, J.; Shak, S.; Ashkenazi A. (1993) Modification of CD4 Immunoadhesin with Monomethoxypoly(ethylene glycol) Aldehyde via Reductive Alkylation, Bioconjugate Chem. 4, 133–140.
6. Merrill, E. W. (1992) Poly(ethylene oxide) and blood contact: A chronicle of one laboratory, pp. 199–220. Poly(ethylene glycol) Chemistry: Biotechnical and Biomedical Applications (J. M. Harris, Ed.), Plenum Press New York.
7. Abuchowski, A.; McCoy, J. R.; Palczuk, N. C.; van Es, T.; Davis, F. F. (1977) Effect of covalent attachment of PEG on immunogenicity and circulating life of bovine liver catalase, J. Biol. Chem. 252, 3582–3586.
8. Jackson, C. J. C.; Charlton, J. L.; Kuzminski, K.; Lang, G. M.; Sehon, A. H. (1987) Synthesis, isolation and characterization of conjugates of ovalbumin with PEG using cyanuric chloride as the coupling agent, Anal. Biochem. 165, 114–127.
9. Koide, A.; Kobayashi, S. (1983) Modification of amino groups in porcine pancreatic elastase with PEG in relation to binding ability towards anti-serum and to enzymatic activity, Biochem Biophys. Res. Commun. 111, 659–667.
10. Nilsson, K.; Mosbach, K. (1984) immobilization of ligands with organic sulfonyl chlorides, Methods Enzymol. 104, 56–69.
11. Delgado, C.; Patel, J. N.; Francis, G. E.; Fisher, D. (1990) Coupling of PEG to albumin under very mild conditions by activation with tresyl chloride: characterization of the conjugate by portioning in aqueous two-phase systems, Biotechnol. Appl. Biochem. 12, 119–128.
12. Buckmann, A. F.; Morr, M.; Johansson, G. (1981) Functionalization of PEG and monomethoxy-PEG, Makromol. Chem. 182, 1379–1384.
13. Joppich, M.; Luisi, P. L. (1979) Synthesis of glycyl-L-tryptophanylglycine substituted by PEG at both carboxy and amino end groups, Makromol. Chem. 180, 1381–1384.

14. Abuchowski, A.; Kazo, G. M.; Verhoesst, C. R., Jr.; Van Es, T.; Kafkewitz, D.; Nucci, M. L.; Viau, A. T.; Davis, F. F. (1984) Cancer therapy with chemically modified enzymes: Anti-tumor properties of PEG-asparaginase conjugates, Cancer Biochem. Biophys. 7, 175–186.

15. Katre, N. V.; Knauf, M. J.; Laird, W. J. (1987) Chemical modification of recombinant interleukin 2 by PEG increases its potency in the murine Meth A sarcoma model, Proc. Natl. Acad. ACi. U.S.A. 84, 1487–1491.

16. Kitamura, N. V.; Takahashi, T.; Yamaguchi, T.; Noguchi, A.; Takashina, K. I.; Tsurumi, H.; Inagake, M.; Toyokuni, T.; Hakamori, S. (1991) Chemical engineering of the monoclonal antibody A7 by polyethylene glycol for targeting cancer chemotherapy, Cancer Res. 51, 4310–4315.

17. Boccu, E.; Largajolli, R.; Veronese, F. M. (1983) Coupling of MePEGs to proteins via active esters, Z. Naturforsch. 38C, 94–99.

18. Zalipsky, S.; Lee, C. (1992) Use of Functionalized PEGs for modification of polypeptides, pp. 347–370. Poly (ethylene glycol) Chemistry: Biotechnical and Biomedical Applications (J. M. Harris, Ed.), Plenum Press New York 1992.

19. Zalipsky, S.; Seltzer, R.; Menon-Rudolph, S. (1992) Evaluation of a new reagent for covalent attachment of PEG to proteins, Biotechnol. Appl. Biochem. 15, 100–114.

20. Veronese, F. M.; Largajolli, R.; Boccu, E.; Benassi, C. A.; Schiavon, O. (1985) Activation of PEG by phenylchloroformates and modification of ribonuclease and superoxide dismutase, Appl. Biochem. Biotech. 11, 141–152.

21. Beauchamp, C. O.; Gonias, S. L.; Menapace, D. P.; Pizzo, S. V. (1983) A new procedure for the synthesis of MePEG-protein adducts: Effects on function, receptor recognition and clearance of superoxide dismutase, lactoferrin and alpha-2-macroglobulin, Anal. Biochem. 131, 25–33.

22. Berger, H.; Pizzo, S. V. (1988) Preparation of polyethylene glycol-tissue plasminogen activator adducts that retain functional activity: Characteristics and behavior in three different species, Blood 71, 1641–1647.

23. Woghiren, C. Sharma, B.; Stein, S. (1993) Protected thiol-polyethylene glycol: A new activated polymer for reversible protein modification, Bioconjugate Chem. 4, 314–318.

24. Byun, Y.; Jacobs, H. A.; Kim, S. W. (1992) Binding kinetics of thrombin and Antithrombin III with immobilized heparin using a spacer, ASAIO Journal, M649-M-653.

25. Use of a poly(propylene)bis-glycidyl ether: Noishiki, Y.; Kodaira, K.; Furuse, M.; Miyata, T. (1989) Method of preparing antithrombogenic medical materials, U.S. Pat. No. 4,806,595

26. Larwood, D.; Szoka, F. (1984) Synthesis, characterization, and in vivo disposition of iodinatable polyethylene glycol derivatives: Differences in vivo as a function of chain length, J. Labelled Comp. Radiopharm. 21, 603.

We claim:

1. A compound of the formula:

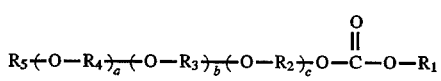

wherein $R_1$ is selected from an N-benzotriazole group, an N-2-pyrrolidinone group, or an 2-oxypyrimidine group; $R_2$, $R_3$ and $R_4$ are independently selected alkylene groups of about 2 to about 3 carbon atoms and may be the same or different; $R_5$ is selected from hydrogen, methyl, a carbonyloxy-N-benzotriazole group, a carbonyloxy-N-2-pyrrolidinone group, and a carbonyl-2-oxypyrimidine group; a is an integer from 1 to 1000 and each of b and c is an integer from 0 to 1000, where a+b+c is an integer from 3 to 1000.

2. A compound of claim 1, where $R_2$, $R_3$ and $R_4$ are independently —$CH_2CH_2$— or —$CH_2CH(CH_3)$— or a combination thereof.

3. A compound of claim 2 wherein $R_2$, $R_3$ and $R_4$ are —$CH_2CH_2$—.

4. A compound of claim 3 wherein $R_5$ is selected so as to give a homobifunctional compound.

5. A method for the covalent bonding of a bioactive compound selected from an aminoglycan polysaccharide, a peptide and a protein to a polymeric surface using a polyoxyalkylene tether which comprises contacting a substrate having an amine-grafted polymeric surface having free amino groups with a compound of claim 1 under conditions whereby said $R_5$ group of the compound of claim 1 reacts with a free amino group of the polymeric surface forming a covalent bond to give a modified polymeric surface having activated polyoxyalkylene groups covalently bonded thereto; and contacting the modified polymeric surface with the bioactive compound, under conditions whereby said bioactive compound is covalently bonded to said tether and wherein said polymeric surface comprises a membrane formed from plasma polymerization of a hydrocyclosiloxane monomer of the general formula

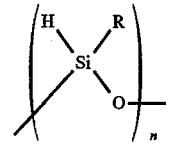

wherein R is an aliphatic group having 1 to about 5 carbon atoms and n is an integer from 2 to about 10.

6. A method according to claim 5 wherein said hydrocyclosiloxane monomer is selected from the group consisting of 1,3,5,7-tetramethylhydrocyclotetrasiloxane, 1,3,5,7,9-pentamethylhydrocyclopentasiloxane, 1,3,5,7,9,11-hexamethylhydrocyclohexasiloxane, and a mixture of 1,3,5,7,9-pentamethylcyclopentasiloxane and 1,3,5,6,9,11-hexamethylcyclohexasiloxane monomers.

7. A method according to claim 6 wherein said free amino groups are grafted on the polymeric surface by reaction with a gas of an N-protected unsaturated or cyclic amine within a plasma chamber under plasma grafting reaction conditions.

8. A method according to claim 7 wherein said N-protected unsaturated or cyclic amine is trimethylsilylallylamine.

9. A method of preparing a thromboresistant coating which comprises
   (a) contacting an object having an amine grafted polymeric surface having primary amine groups with a compound of claim 1; and
   (b) contacting the object with a solution of heparin, wherein said polymeric surface comprises a membrane formed from plasma polymerization of a hydrocyclosiloxane monomer of the general formula

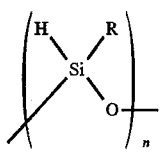

where R is an aliphatic group having 1 to about 5 carbon atoms and n is an integer from 2 to about 10.

10. A thromboresistant coating made by the method of claim 9.

11. A thromboresistant coating which comprises a membrane formed from the plasma polymerization of hydrocyclosiloxane monomer of the general formula:

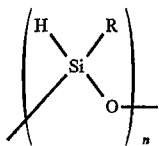

where R is an aliphatic group having 1 to about 5 carbon atoms and n is an integer from 2 to about 10, covalently linked by a carbamate linkage to one end of a polyoxyalkylene tether wherein the tether is covalently linked at its other end by a carbamate linkage to a heparin molecule, which is prepared by coupling a compound of claim 1 with a free amine group of the membrane, followed by coupling to heparin.

12. A thromboresistant coating according to claim 11 wherein said hydrocyclosiloxane monomer is selected from the group consisting of 1,3,5,7-tetramethylhydrocyclotetrasiloxane, 1,3,5,7,9-pentamethylhydrocyclopentasiloxane, 1,3,5,7,9,11-hexamethylhydrocyclohexasiloxane, and a mixture of 1,3,5,7,9-pentamethylcyclopentasiloxane and 1,3,5,6,9,11-hexamethylcyclohexasiloxane monomers.

13. A thromboresistant coating according to claim 12 wherein said polyoxyalkylene tether is a polyethyleneglycol.

14. A thromboresistant coating according to claim 13 wherein said polyethylene glycol has a molecular weight of about 500 to 20,000.

15. A substrate polymeric coating having a bioactive compound covalently attached by a polyoxyalkylene tether to the polymeric surface which comprises a membrane formed from the plasma polymerization of hydrocyclosiloxane monomer of the general formula:

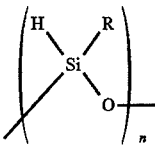

where R is an aliphatic group having 1 to about 5 carbon atoms and n is an integer from 2 to about 10, covalently linked by a carbamate linkage to one end of a polyoxyalkylene tether wherein the tether is covalently linked at its other end by a carbamate linkage to a bioactive molecule, which is prepared by coupling a compound of claim 1 with a free amine group of the membrane, followed by coupling to the bioactive molecule.

16. A coating according to claim 15 wherein said bioactive compound is selected from the group consisting of an aminoglycan polysaccharide, a polypeptide, a protein, a compound halving antithrombotic or thrombolytic properties and a metal chelator.

17. A coating according to claim 16 wherein said bioactive compound is selected from the group consisting of heparin, tissue plasminogen activator, streptokinase, a prostaglandin, an antiplatelet drug and deferoxamine.

18. A coating according to claim 15 wherein said hydrocyclosiloxane monomer is selected from the group consisting of 1,3,5,7-tetramethylhydrocyclotetrasiloxane, 1,3,5,7,9-pentamethylhydrocyclopentasiloxane, 1,3,5,7,9,11-hexamethylhydrocyclohexasiloxane, and a mixture of 1,3,5,7,9-pentamethylcyclopentasiloxane and 1,3,5,6,9,11-hexamethylcyclohexasiloxane monomers.

19. A coating according to claim 18 wherein said polyoxyalkylene tether is a polyethyleneglycol.

20. A coating according to claim 19 wherein said polyethylene glycol has a molecular weight of about 500 to 20,000.

21. A modified polymeric surface made according to the method of claim 5.

* * * * *